(12) United States Patent
Yang

(10) Patent No.: US 7,896,004 B2
(45) Date of Patent: Mar. 1, 2011

(54) TRACHAEL INTUBATION TUBE FIXING DEVICE WITH SUCTION TUBE INSERTION OPENING

(75) Inventor: Ju-Seok Yang, Seoul (KR)

(73) Assignee: Unimedics Co., Ltd., Seoul (KR)

( * ) Notice: Subject to any disclaimer, the term of this patent is extended or adjusted under 35 U.S.C. 154(b) by 811 days.

(21) Appl. No.: 11/870,073

(22) Filed: Oct. 10, 2007

(65) Prior Publication Data

US 2008/0087281 A1 Apr. 17, 2008

(30) Foreign Application Priority Data

Oct. 11, 2006 (KR) .................. 10-2006-0098820
Apr. 10, 2007 (KR) .................. 20-2007-0005875 U

(51) Int. Cl.
*A61M 11/00* (2006.01)

(52) U.S. Cl. ............................ 128/200.26; 128/207.17

(58) Field of Classification Search ..............................
128/207.15–207.17, DIG. 26, 200.26
See application file for complete search history.

(56) References Cited

U.S. PATENT DOCUMENTS

| | | | |
|---|---|---|---|
| 4,832,019 A | 5/1989 | Weinstein | |
| 5,069,206 A * | 12/1991 | Crosbie | 128/207.17 |
| 5,934,276 A * | 8/1999 | Fabro et al. | 128/207.17 |
| 6,763,831 B2 * | 7/2004 | Sniadach | 128/206.29 |
| 7,063,088 B1 * | 6/2006 | Christopher | 128/207.17 |
| 7,628,154 B2 * | 12/2009 | Bierman et al. | 128/207.17 |

FOREIGN PATENT DOCUMENTS

| | | |
|---|---|---|
| KR | 20-2002-0022115 | 11/2001 |
| KR | 20-2004-007232 | 6/2004 |
| KR | 20-2004-0009696 | 7/2004 |

\* cited by examiner

*Primary Examiner*—Steven O Douglas
(74) *Attorney, Agent, or Firm*—Edwards Angell Palmer & Dodge LLP; Kongsik Kim, Esq.

(57) ABSTRACT

Disclosed is a tracheal intubation tube fixing device for securing an airway in the patient's respiratory tract and inducing the artificial respiration of a patient in the intensive care unit or under a general anesthesia operation. The device includes a body to surround the patient's face and mouth and including an airway securing block, a suction tube insertion opening, an intubation tube insertion hole and band fixing holes, a pivotal fixing member to fix an inserted intubation tube, a coupling structure to assure free entrance and exit of the pivotal fixing member into and out of the intubation insertion hole, a padding member attached to Velcro tapes of the body, and a holding member configured to closely surround the patient's rear neck and coupled to the body via the band fixing holes to prevent the body from being moved from a wearing position thereof.

15 Claims, 16 Drawing Sheets

TRACHAEL INTUBATION TUBE FIXING DEVICE WITH SUCTION TUBE INSERTION OPENING

CROSS-REFERENCE TO RELATED APPLICATION

The present application claims, under 35 U.S.C. §119, the benefit of Korean Patent Application No. 10-2006-0098820, filed Oct. 11, 2006 and Korean Patent Application No. 20-2007-0005875, filed Apr. 10, 2007, the entire contents of which are hereby incorporated by reference.

BACKGROUND

1. Technical Field

The present invention relates to a tracheal intubation tube fixing device with a suction tube insertion opening, and more particularly, to a fixing device for a tracheal intubation tube, which can be used to secure an airway in the patient's respiratory tract and to induce the artificial respiration of a serious patient in the intensive care unit as well as the respiration of a patient under a general anesthesia operation, for the sake of protecting the patient's life.

2. Background Art

In general, a tracheal intubation tube is inserted into the trachea of a patient, for example, under a general anesthesia operation or in the intensive care unit, to induce the patient's artificial respiration under the assistance of an artificial respirator and to secure an airway in the patient's respiratory tract in the event of an emergency. In use, after a tracheal intubation tube is inserted into the trachea by an appropriate length, an adhesive tape is wound on the tube and attached around the patient's mouth to fix the tracheal intubation tube without the risk of separation.

With the above described fixing method of the tracheal intubation tube, however, since the tube is loosely fixed to the patient's mouth, the tube may be easily removed from the respiratory tract, or the patient may consciously or unconsciously pull out the tube with his/her hand. This makes it impossible for the tube to secure an airway in the patient's respiratory tract, causing a serious situation.

In particular, in the case of an infant, the tube is easily separated from the trachea even by a slight movement thereof, causing an emergency. Also, due to the use of the adhesive tape, a patient having weak skin may suffer from contact dermatitis.

Further, in view of healing and nursing, since fixing of the tube using the adhesive tape normally requires cooperation of two persons to insert the tube into the trachea and to fix the inserted tube, there is the problem of waste of labor. Also, when it is desired to insert a suction tube into the trachea for removing secretion such as phlegm, etc. in the trachea, it is difficult to secure an airway in the respiratory tract. In addition, there is the risk that the tube shakes and is separated from the trachea when the patient moves his/her neck, etc. due to pain upon a forcible insertion of the tube and upon the removal of the secretion, and the tube may be unintentionally separated from the patient's trachea as the adhesive tape is released by the patient's spit and secretion.

In addition, the tube inserted into the trachea can be pushed by the patient's teeth. As a result, it can fail to secure an airway in the respiratory tract. Also, the patient's mouth and teeth, etc. can be injured upon insertion of the tube, which can result in a secondary infection by infiltration of bacteria and pathogens.

The information disclosed in this Background section is only for enhancement of understanding of the background of the invention and should not be taken as an acknowledgement or any form of suggestion that this information forms the prior art that is already known to a person skilled in the art.

SUMMARY

Therefore, the present invention has been made in view of the above-described problems, and it is an object of the present invention to provide a tracheal intubation tube fixing device, wherein, after a semi-arcuate body of the device is worn on the patient's face and an airway securing block of the body is inserted into the patient's mouth to rapidly secure an airway in the respiratory tract, a holding member is coupled to the body as both ends thereof are fitted into band fixing holes formed in both ends of the body, to closely surround the patient's rear neck so as to fix the body to the patient's face while preventing the body from being unintentionally moved from an accurate wearing position thereof, and for the sake of protecting the patient's life, a tracheal tube can be rapidly and easily inserted into the patient's respiratory tract and be fixed using a pivotal fixing member so as to secure an airway in the respiratory tract, and the body is formed with a suction tube insertion opening to enable the efficient removal of secretion such as phlegm, etc. in the trachea and to induce the artificial respiration of a serious patient in the intensive care unit as well as the respiration of a patient under a general anesthesia operation, and in addition, a padding member is seated on an inner surface of the body to protect the patient's face by absorbing a pressure applied from the body to the patient's face while preventing skin trouble.

In accordance with an aspect of the present invention, the above and other objects can be accomplished by the provision of a tracheal intubation tube fixing device having a suction tube insertion opening for securing an airway in the patient's respiratory tract comprising: a body configured to surround the patient's face and mouth and including an airway securing block to be inserted into the mouth, the suction tube insertion opening for the insertion of a suction tube, an intubation tube insertion hole for the insertion of an intubation tube, and band fixing holes; a pivotal fixing member to maintain the intubation tube, inserted into the intubation insertion hole, at a fixed position; a coupling structure to be coupled with the pivotal fixing member so as to assure free entrance and exit of the pivotal fixing member into and out of the intubation insertion hole; a padding member having a surface to be attached to Velcro tapes provided at both ends of the body; and a holding member configured to closely surround the patient's rear neck, the holding member being coupled to the body as being fitted, at both ends thereof, into the band fixing holes to prevent the body from being moved from a wearing position thereof.

In a preferred embodiment, the pivotal fixing member may comprise: a pivoting piece having a first pivoting contact surface formed along an outer periphery thereof, a semi-arcuate guide groove recessed in a surface thereof to be opened at one end thereof, a coupling protrusion formed at the same surface as the guide groove to be positioned eccentric to the center thereof, and a pivoting grip formed at a lower end thereof; and a fixing piece including a body piece and a contact piece closely coupled with each other, the body piece having a pivoting shaft to be coupled with an inner circumferential wall of the guide groove and a second pivoting contact surface to come into close contact with the first pivoting contact surface in a pivoting direction of the pivoting piece, and the contact piece having a coupling hole to be coupled with a coupling head protruding from the body piece.

In another preferred embodiment, the coupling structure may comprise: a pair of coupling shafts having first and second coupling holes, respectively; a coupling bar to be penetrated through the first and second coupling holes, if the coupling protrusion of the pivotal fixing member being inserted into a space between the first and second coupling holes, the coupling protrusion being coupled with the first and second coupling holes by means of the coupling bar penetrated through the first and second coupling holes; and an insertion wall portion defining the intubation tube insertion hole and having a guide hole perforated in a position thereof between the shafts, to facilitate entrance and exit of the body piece, the insertion wall portion having a predetermined height starting from a plane having the insertion hole.

In the above embodiment, the first pivoting contact surface of the pivoting piece may, preferably, be formed with a plurality of first corrugations, to prevent unwanted movement of the pivoting piece when the pivoting piece is pivotally rotated to come into close contact with the intubation tube for the fixing of the tracheal tube and to assure the close contact/fixing of the pivoting piece with various sizes of the tracheal tube, and the second pivoting contact surface to come into contact with the first pivoting contact surface may, suitably, be formed with a plurality of second corrugations to be engaged with the first corrugations, so as to assure the close contact/fixing of the intubation tube and the fixing piece.

Also in the above embodiment, the contact piece may serve to maintain the circular shape of the intubation tube when the intubation tube comes into close contact with and is fixed by the pivotal fixing member, and comprises a contact recess to facilitate the close contact/fixing of the circular intubation tube. Preferably, the intubation tube insertion hole may be opened at a peripheral position thereof to facilitate the insertion and close contact/fixing of the intubation tube.

In still another preferred embodiment, the suction tube insertion opening may have a heart shape.

In a further preferred embodiment, the airway securing block may be made of a micro-foam material to prevent any injury on the patient's teeth and mouth caused when the airway securing block is inserted into the patient's mouth for the purpose of securing an airway in the respiratory tract.

In yet a further preferred embodiment, the padding member may comprise a padding body portion, and the padding body portion may have: a suction tube insertion hole perforated in a position thereof corresponding to the suction tube insertion opening for the insertion of the suction tube; an airway securing block penetrating hole for the penetration of the airway securing block; and an intubation tube insertion hole perforated in a position thereof corresponding to the intubation tube insertion hole of the body, the intubation tube insertion hole of the padding body portion being opened at a peripheral position thereof.

In the above embodiment, the padding body portion of the padding member may include a plurality of layers, and the plurality of layers may include: an air-permeable sponge layer to absorb a pressure applied from the body to the patient's face and mouth; an air-permeable non-woven fabric seating layer attached to one surface of the sponge layer, to be seated on the inner surface of the body; and an air-permeable non-woven fabric contact layer attached to the other surface of the sponge layer, to come into contact with the patient's face and mouth. Preferably, the contact layer of the padding member may have a plurality of vent holes.

In yet another preferred embodiment, the holding member may comprise: a body portion to closely surround the patient's rear neck; a pair of supporter portions extending from both ends of the body portion by a predetermined length; and a pair of connectors provided at one end of the respective supporter portions, to be fitted into to the band fixing holes of the body. Preferably, the body portion and the supporter portions of the holding member may be formed by laminating air-permeable non-woven fabrics in multiple layers.

In the above embodiment, each connector of the holding member may, preferably, have one end coupled to one end of the associated supporter portion and the other end provided at a surface thereof with a Velcro tape such that the other end of the connector is attached to a surface of the supporter portion after being fitted into the associated band fixing hole of the body.

The above preferred embodiments of the present invention provide advantageous effects including the following.

Firstly, after a semi-arcuate body of the device is worn on the patient's face and is fixed by a holding member, an airway securing block formed at the body is inserted into the patient's mouth, to rapidly secure an airway in the patient's respiratory tract in a convenient manner. Accordingly, a rapid emergency response for a serious patient can be conveniently and safely accomplished, resulting in an increase in the viability of the patient.

Secondly, since the airway securing block formed at the body can secure a sufficient airway in the respiratory tract, a tracheal tube can be rapidly and conveniently inserted into the patient's trachea, enabling a rapid emergency response.

Thirdly, the inserted tracheal tube can be fixed close to the patient's mouth by use of a pivotal fixing member. This has the effects of simplifying a manual tube fixing operation and reducing the waste of labor required to fix the tube. In particular, even if a patient consciously or unconsciously pulls out the inserted tube, there is no risk of the tube being separated from the trachea to fall the patient into a dangerous situation.

Fourthly, since the patient's life may be in danger when secretion such as phlegm, etc. generated in the patient's respiratory tract closes the respiratory tract, there is a need to insert a suction tube into the respiratory tract to secure an airway. For this, the body is formed with a suction tube insertion opening to suction remove the secretion such as phlegm, etc. With this configuration, the suction tube and the tracheal tube can be inserted together, to simultaneously perform their operations. That is, since an operator can freely perform an operation for removing the secretion such as phlegm, etc. using the suction tube without paying an attention to the fixed tracheal tube, it is possible to reduce the waste of labor.

Fifthly, the airway securing block to be inserted into the patient's mouth for securing an airway in the respiratory tract is made of a soft micro-foam material. This has the effect of preventing an injury on the patient's mouth and teeth, and consequently, a secondary infection caused by infiltration of bacteria and pathogens.

Other aspects of the present invention are discussed infra.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figure 1:
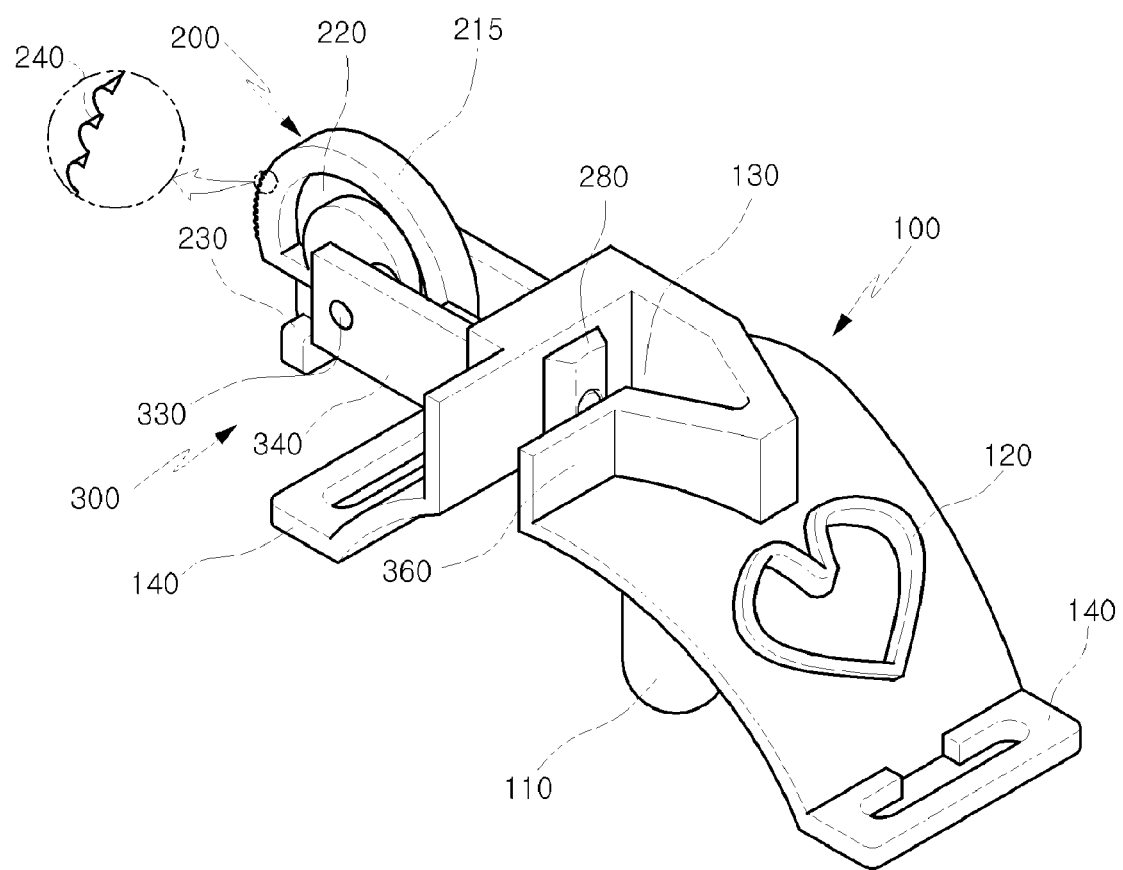
FIG. 1 is a perspective view of a tracheal intubation tube fixing device having a suction tube insertion opening according to the present invention.

Reference will now be made in detail to the preferred embodiment of the present invention, examples of which are illustrated in the drawings attached hereinafter, wherein like reference numerals refer to like elements throughout. The embodiments are described below so as to explain the present invention by referring to the figures.

Figure 2:
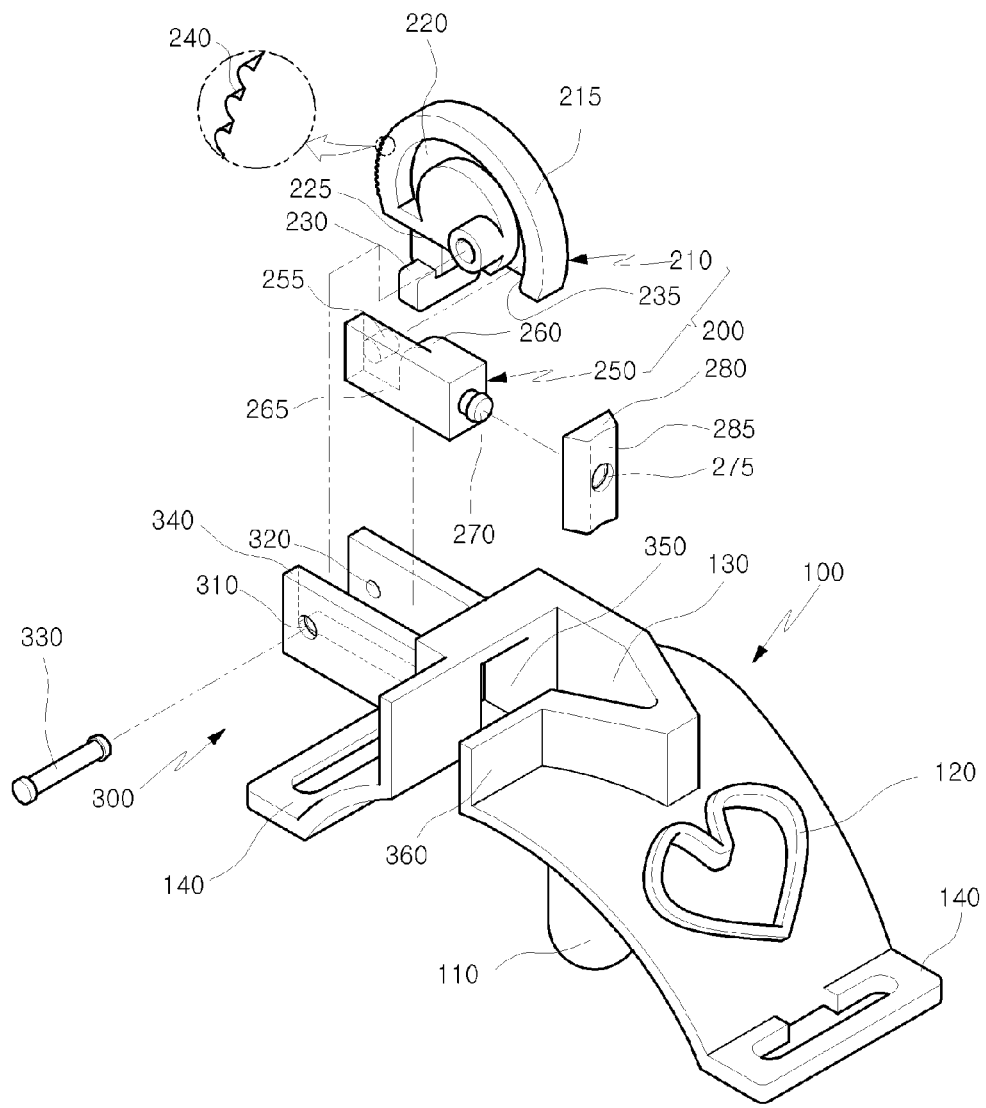
FIG. 2 is an exploded perspective view of the tracheal intubation tube fixing device having the suction tube insertion opening shown in FIG. 1.
Figure 3:
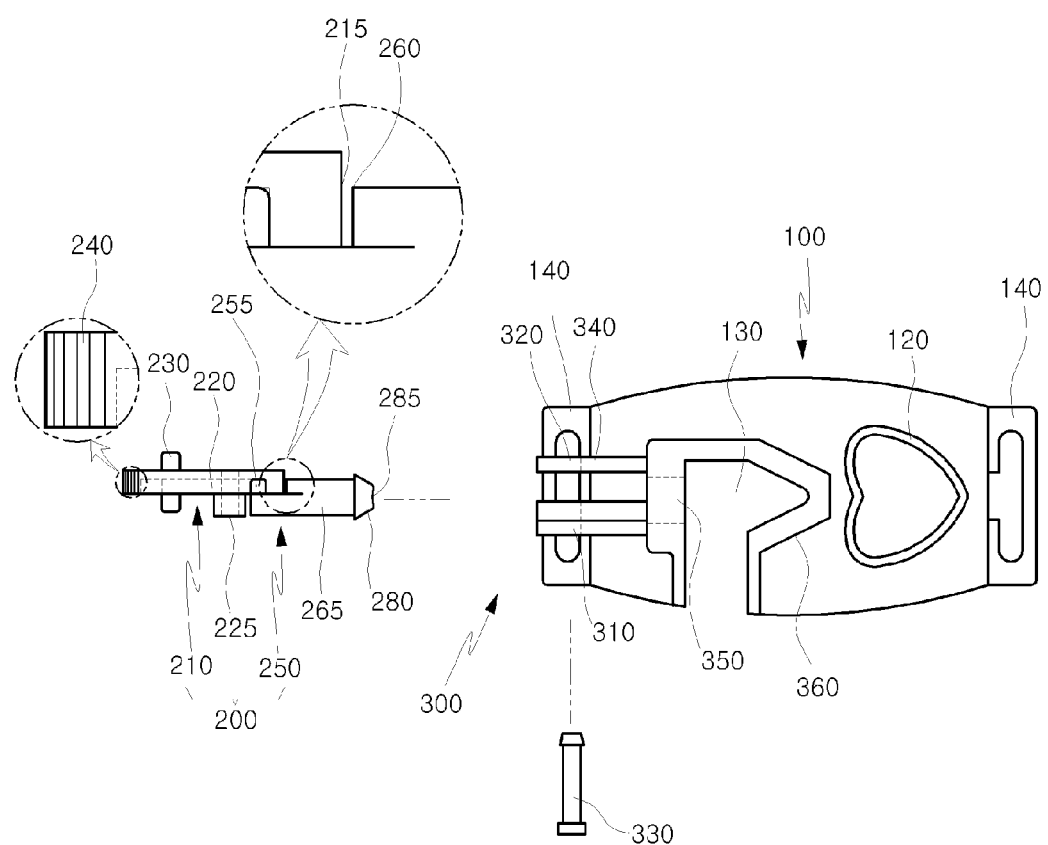
FIG. 3 is a plan view illustrating a pivotable fixing member and a body of the tracheal intubation tube fixing device according to the present invention.
Figure 4:
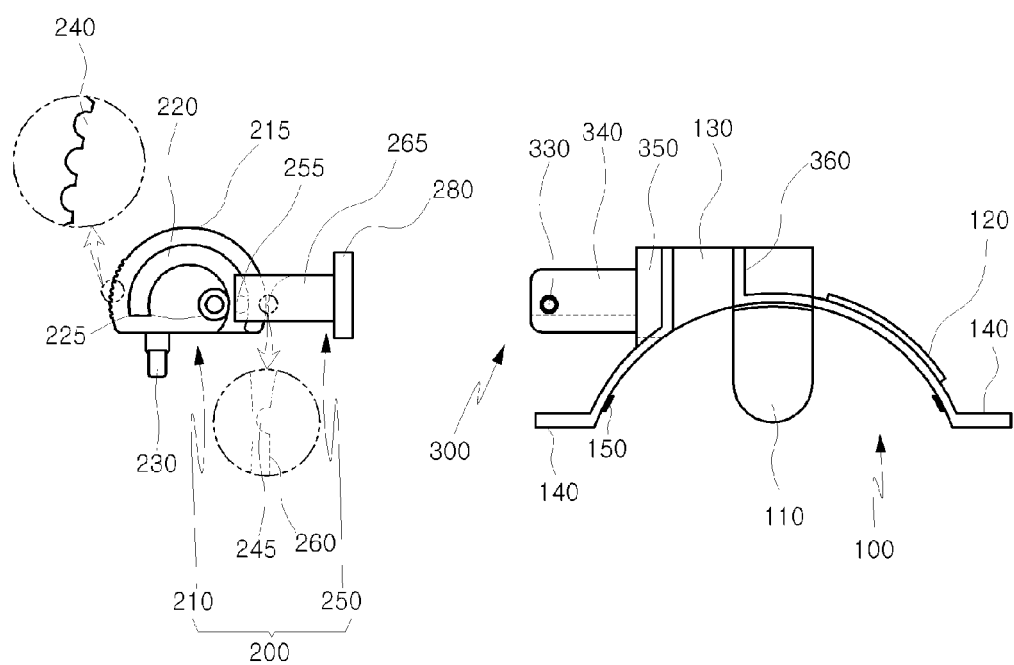
FIG. 4 is front view of the pivotable fixing member and the body shown in FIG. 3.
Figure 5:
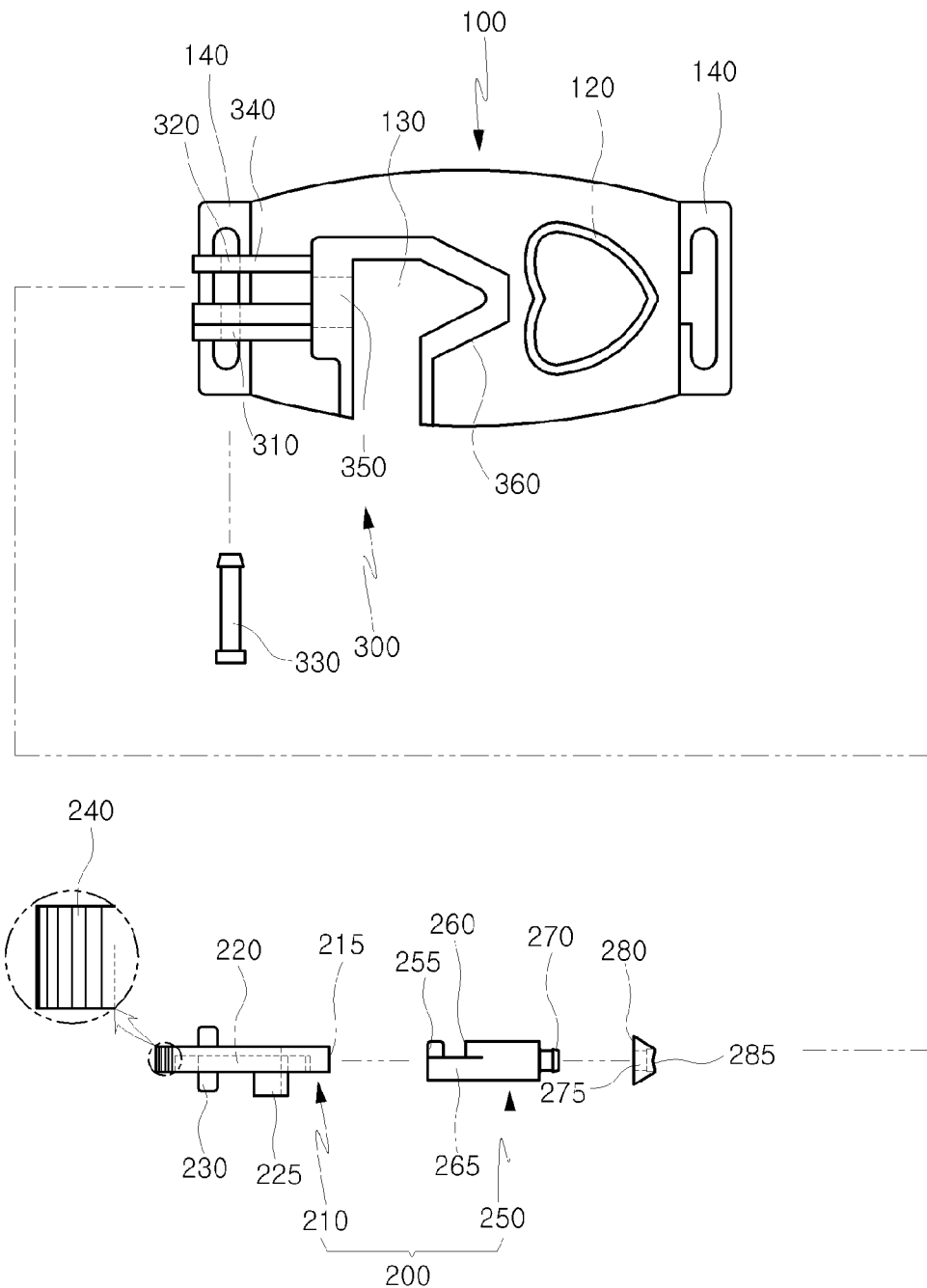
FIG. 5 is an exploded plan view of the tracheal intubation tube fixing device having the suction tube insertion opening.
Figure 6:
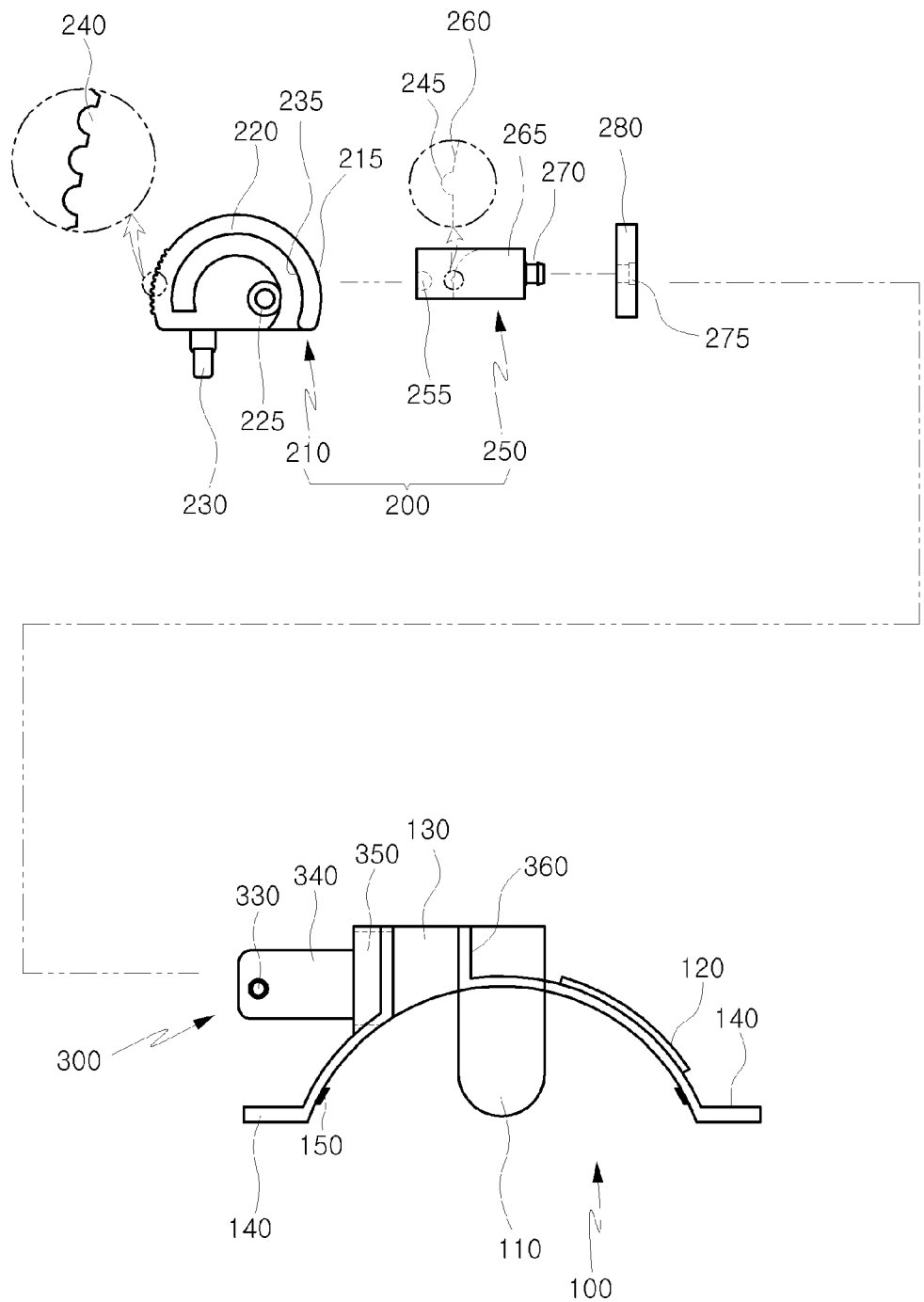
FIG. 6 is an exploded front view of the tracheal intubation tube fixing device having the suction tube insertion opening.
Figure 7:
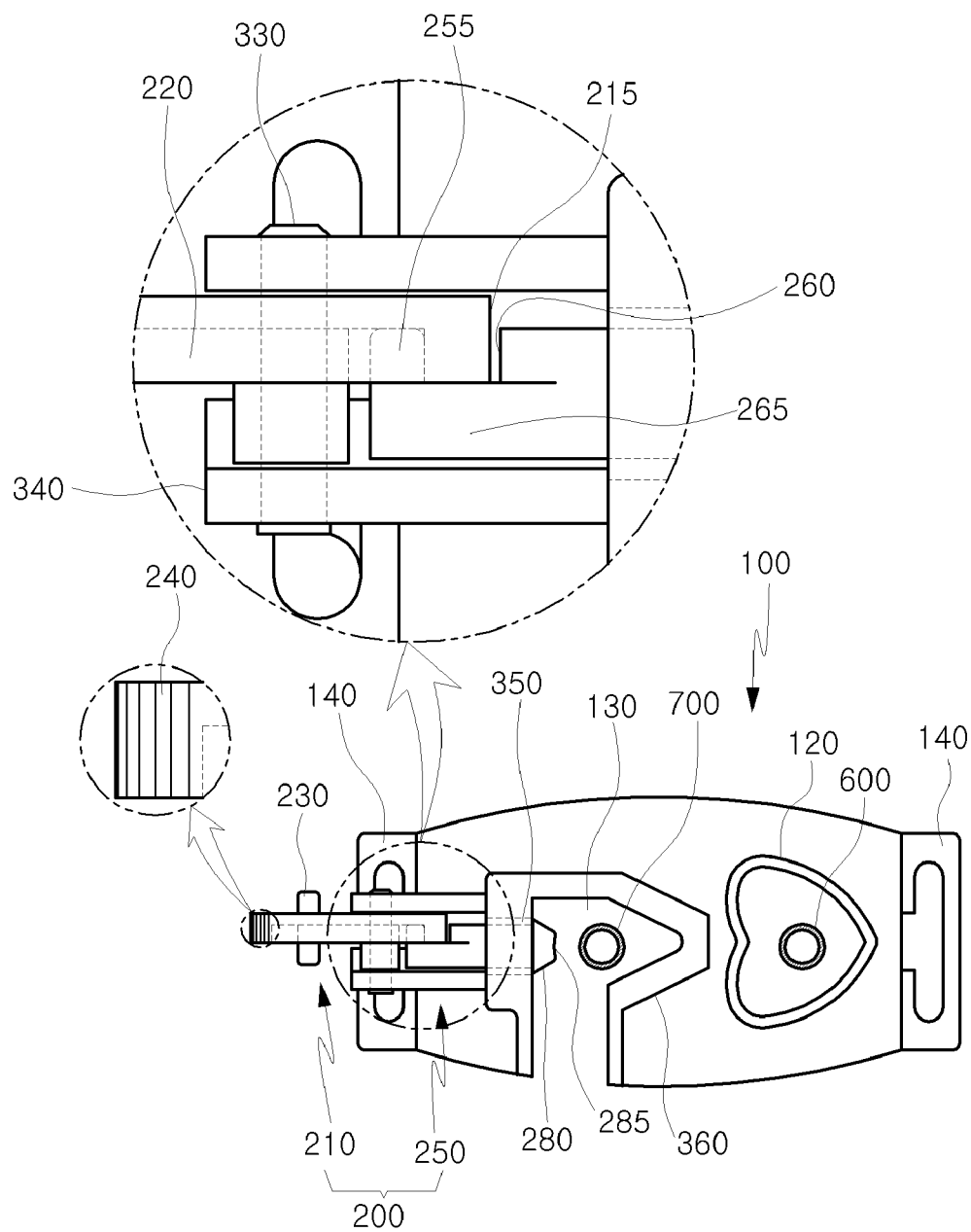
FIG. 7 is a plan view illustrating the assembled tracheal intubation tube fixing device having the suction tube insertion opening.
Figure 8:
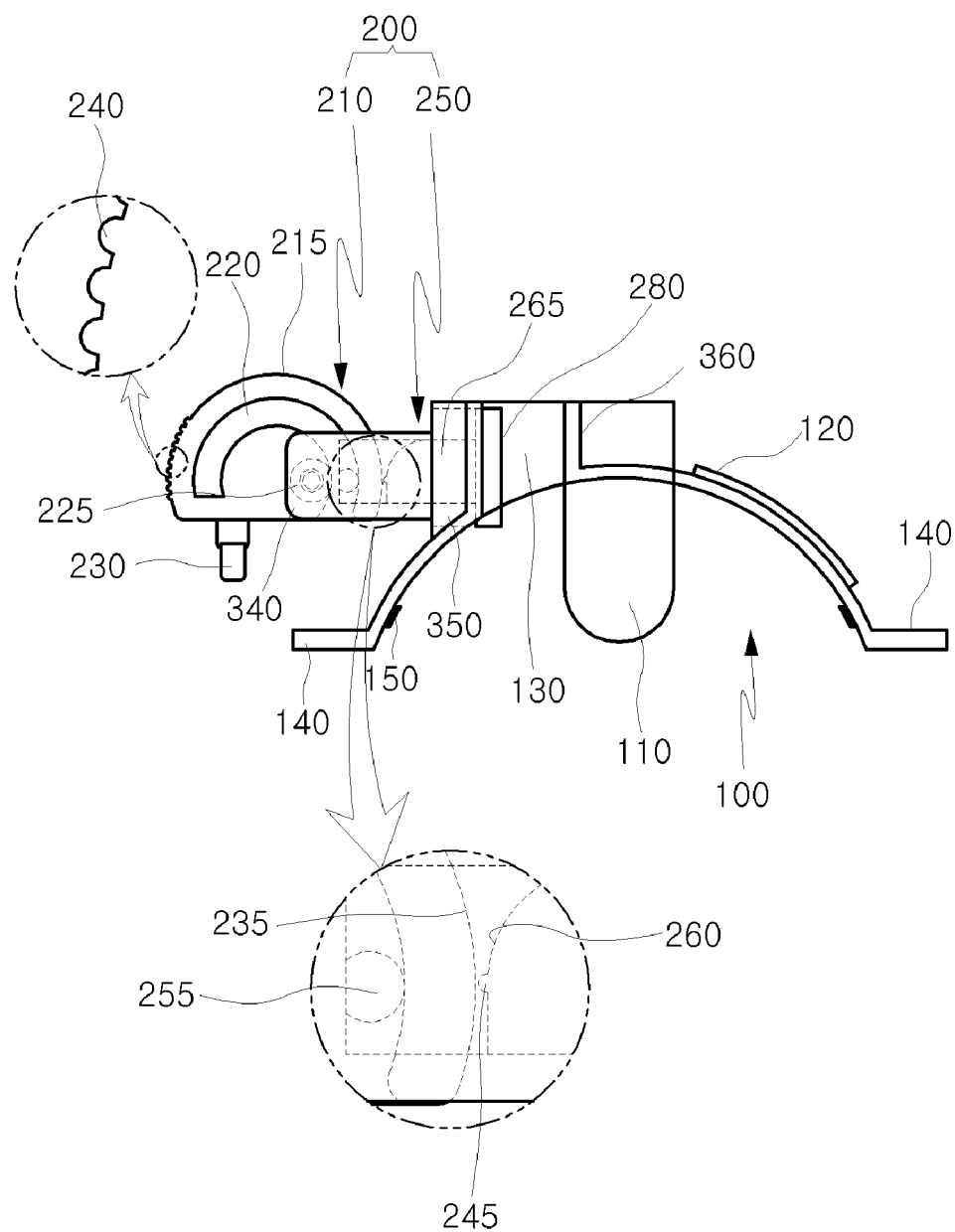
FIG. 8 is a front view of the assembled tracheal intubation tube fixing device having the suction tube insertion opening.
Figure 9:
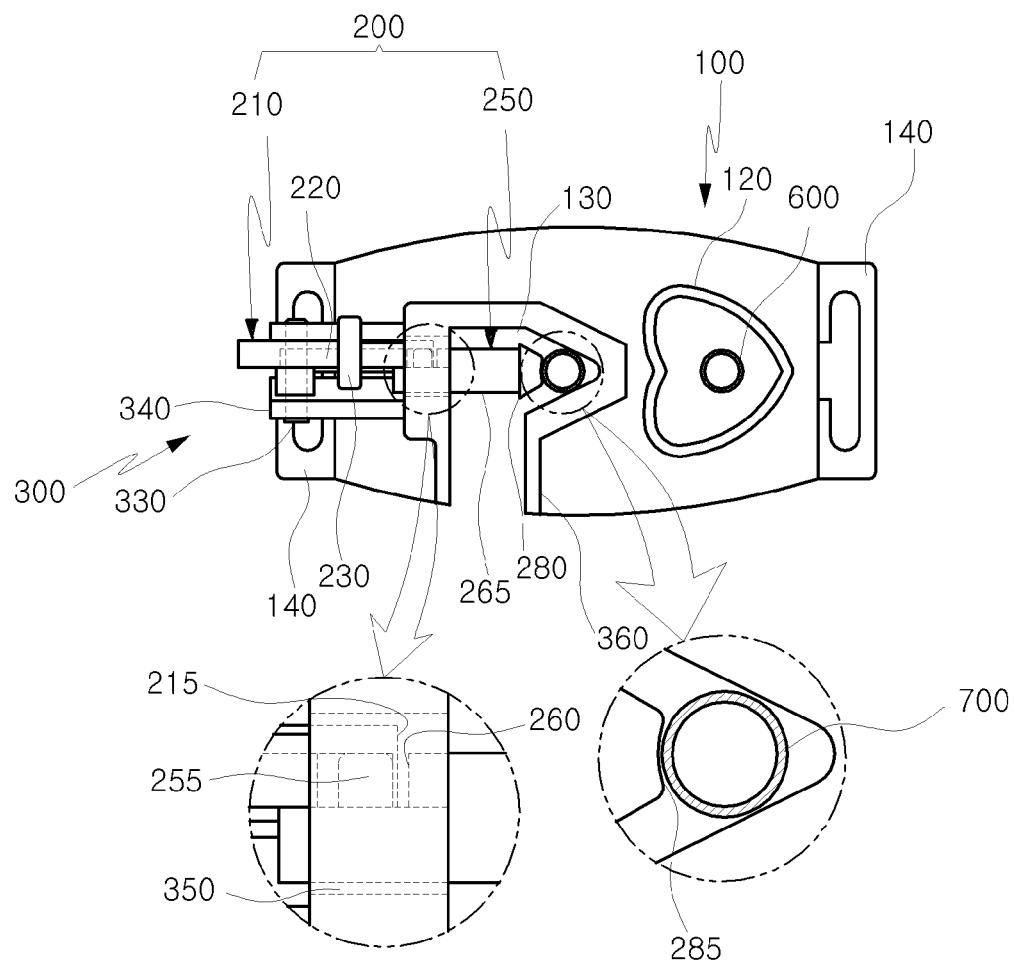
FIG. 9 is a plan view illustrating the use state of the tracheal intubation tube fixing device having the suction tube insertion opening.
Figure 10:
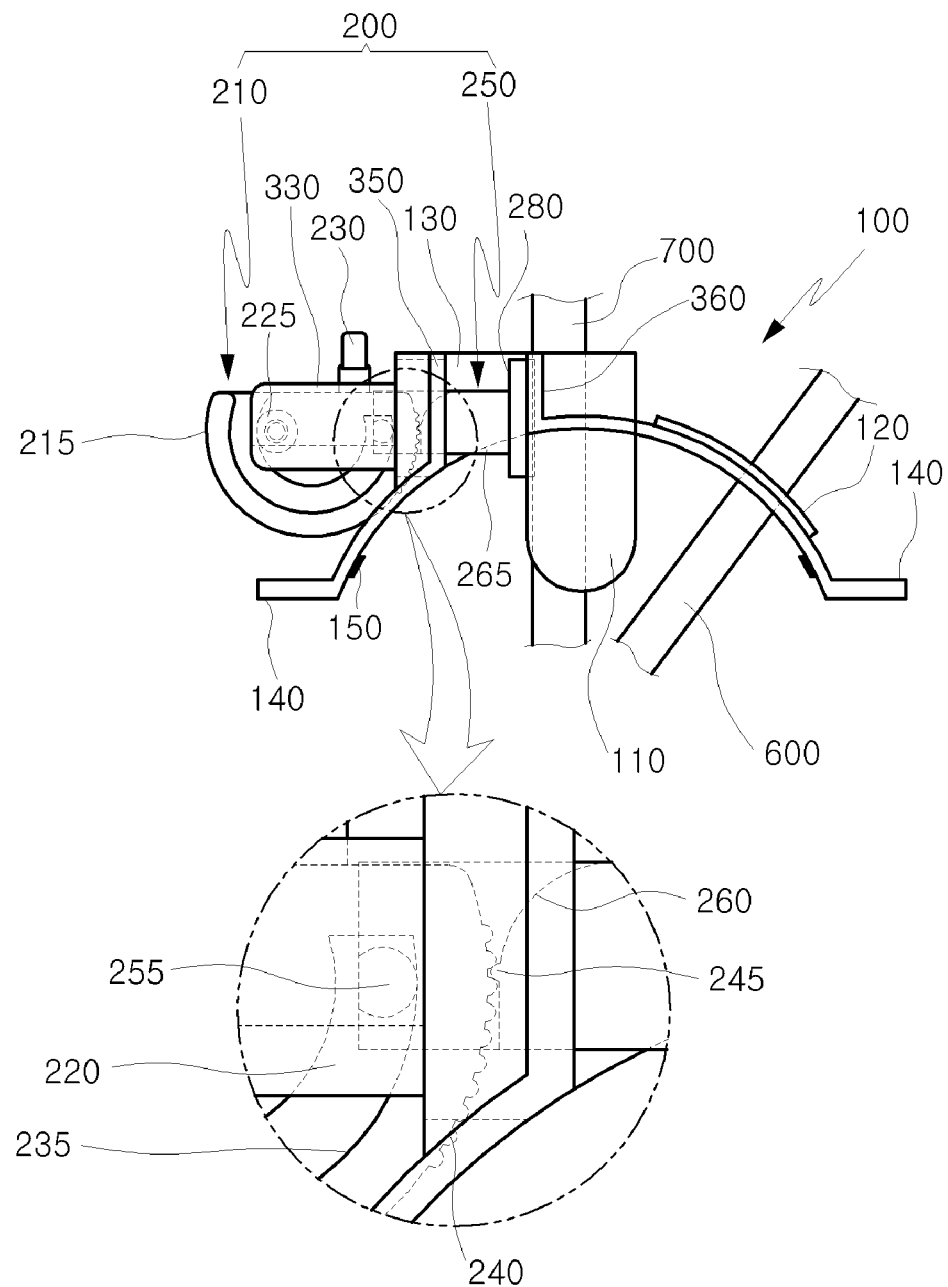
FIG. 10 is a front view of the tracheal intubation tube fixing device having the suction tube insertion opening shown in FIG. 9.
Figure 11:
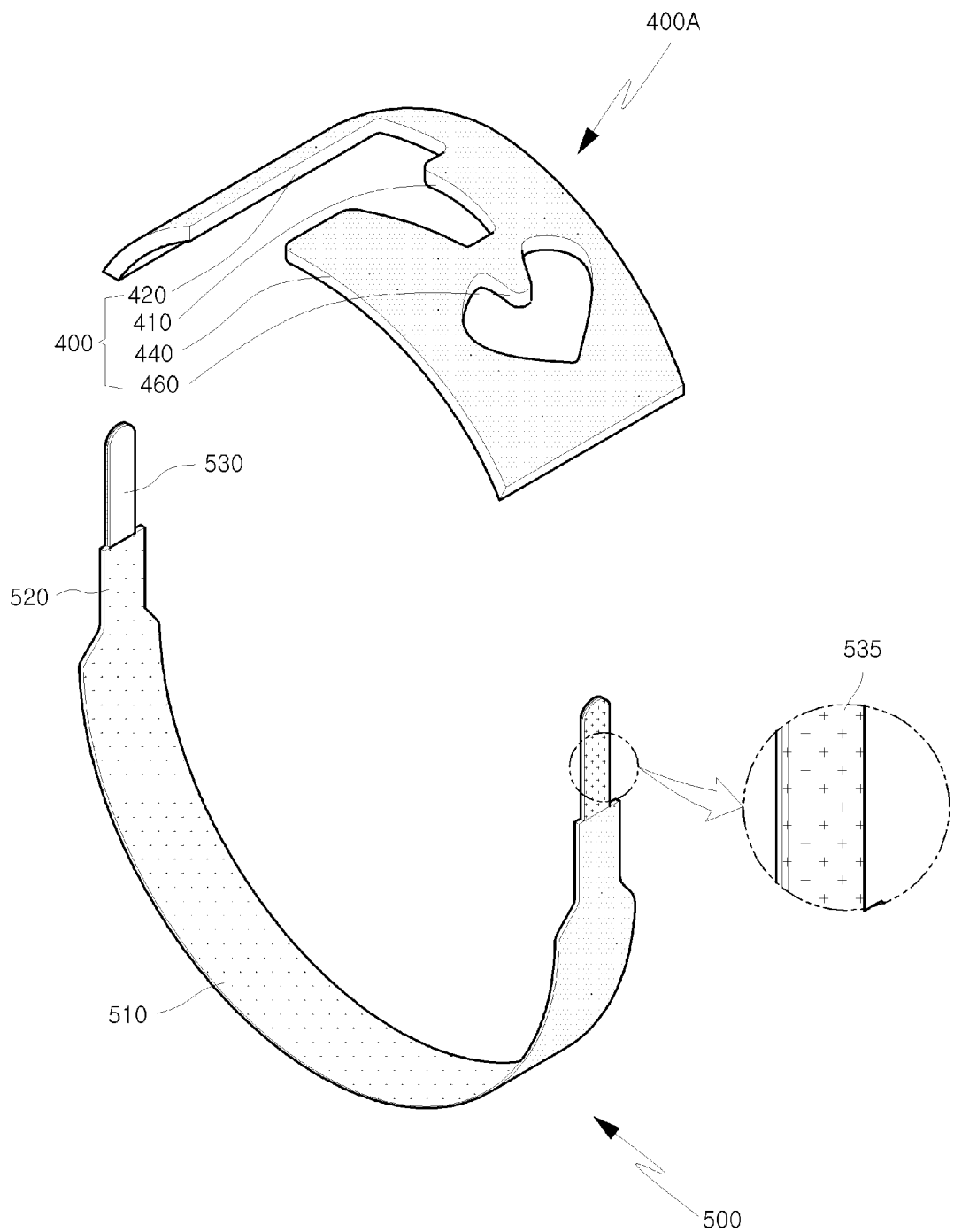
FIG. 11 is a perspective view illustrating a padding member and a holding member of the tracheal intubation tube fixing device having the suction tube insertion opening according to the present invention.
Figure 12:
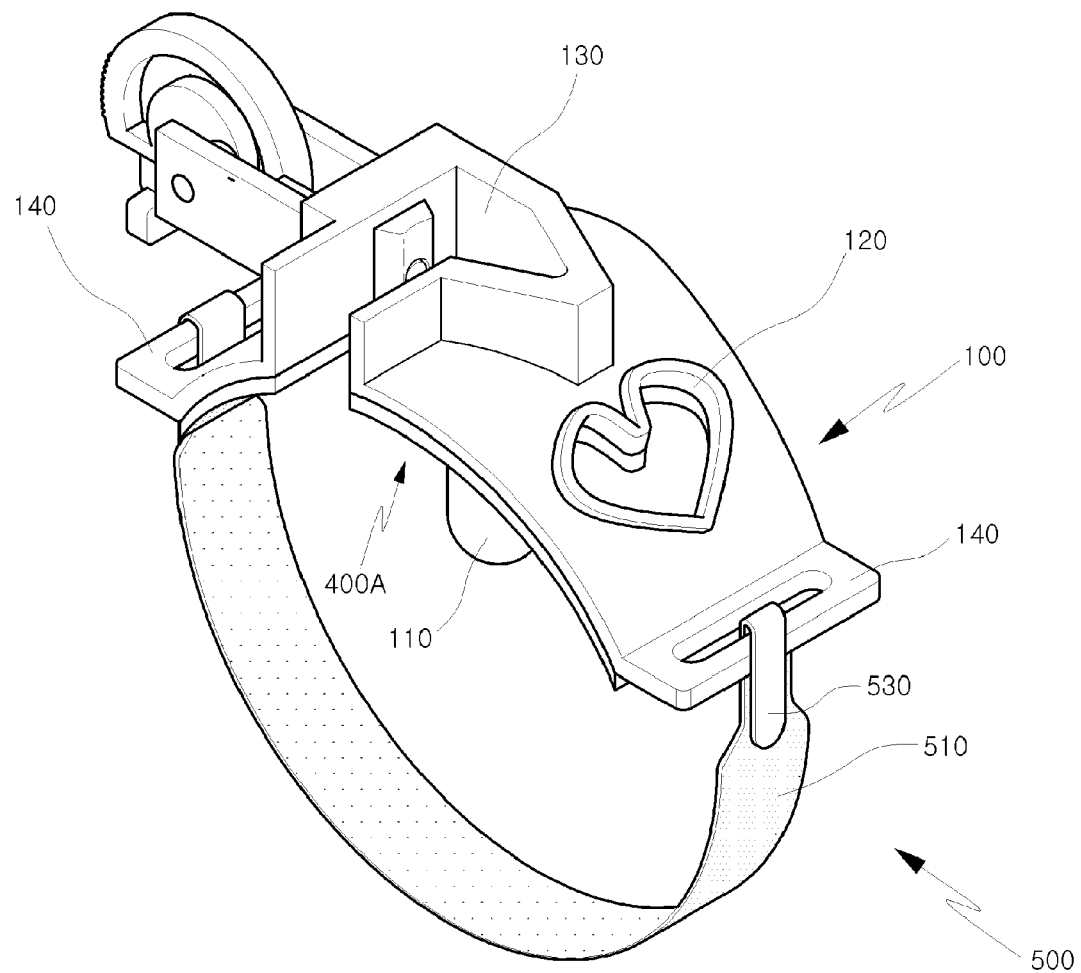
FIG. 12 is a perspective view illustrating the padding member and the holding member shown in FIG. 11, which are coupled to the body of the tracheal intubation tube fixing device having the suction tube insertion opening.
Figure 13:
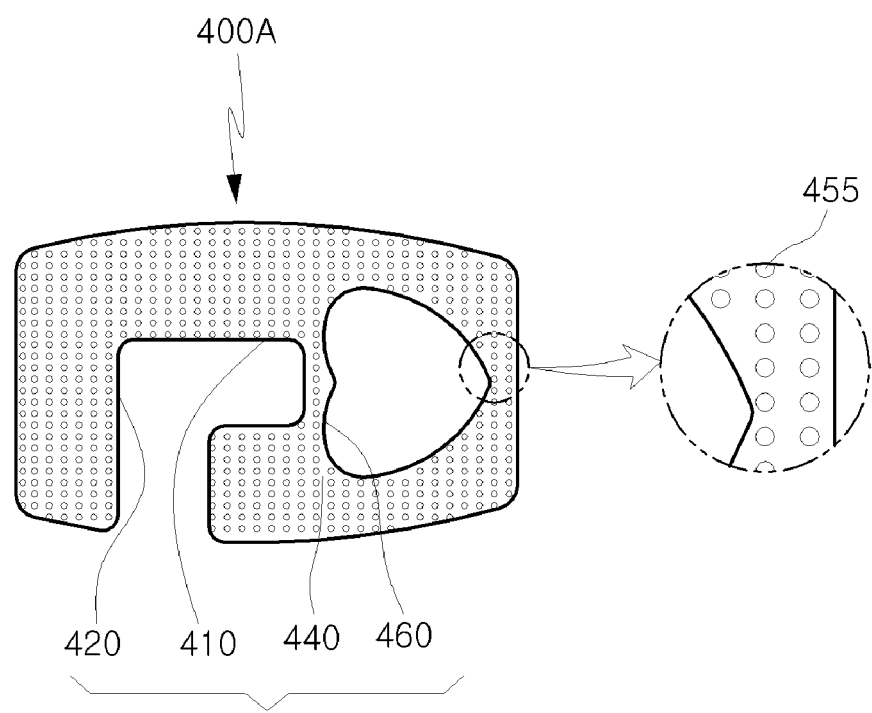
FIG. 13 is a plan view illustrating a contact portion of the padding member of the tracheal intubation tube fixing device.
Figure 14:
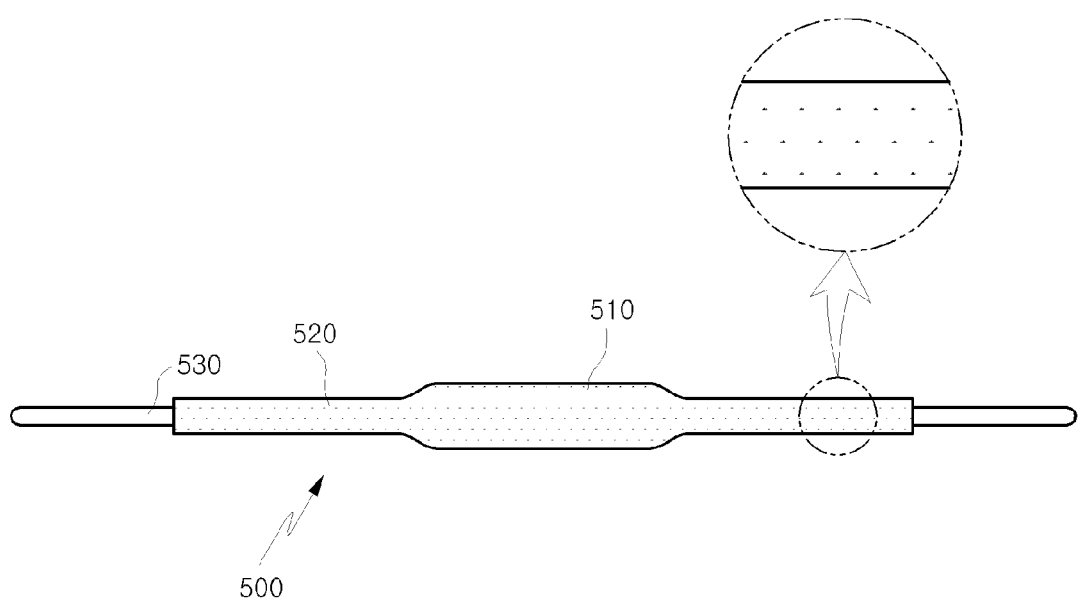
FIG. 14 is a plan view illustrating the holding member of the tracheal intubation tube fixing device.
Figure 15:
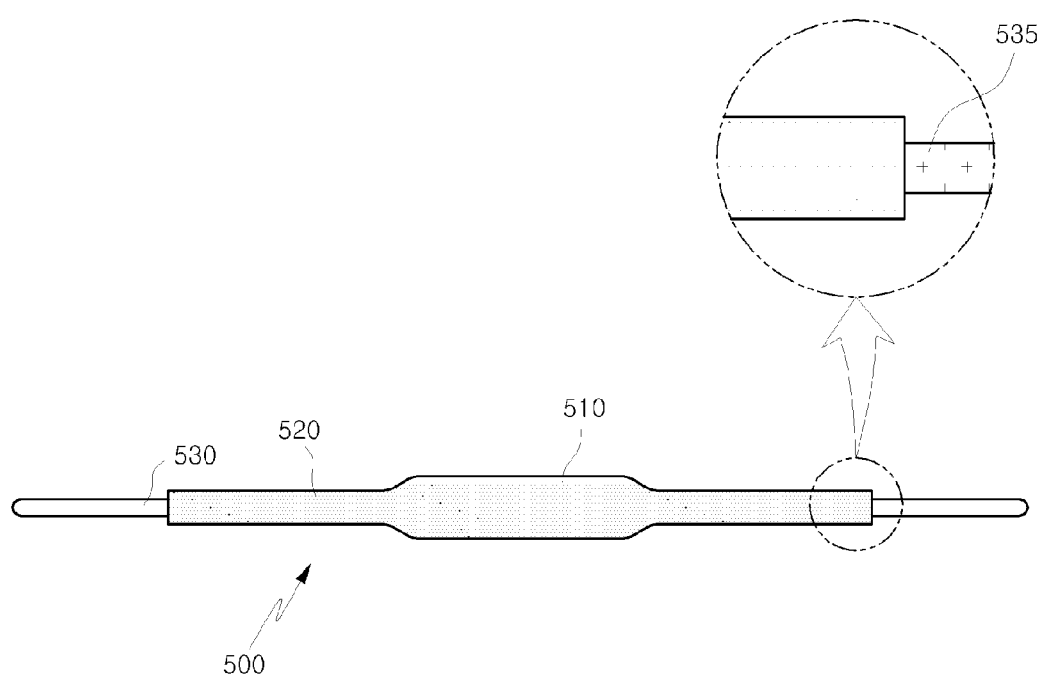
FIG. 15 is a plan view illustrating a connector included in the holding member.
Figure 16:
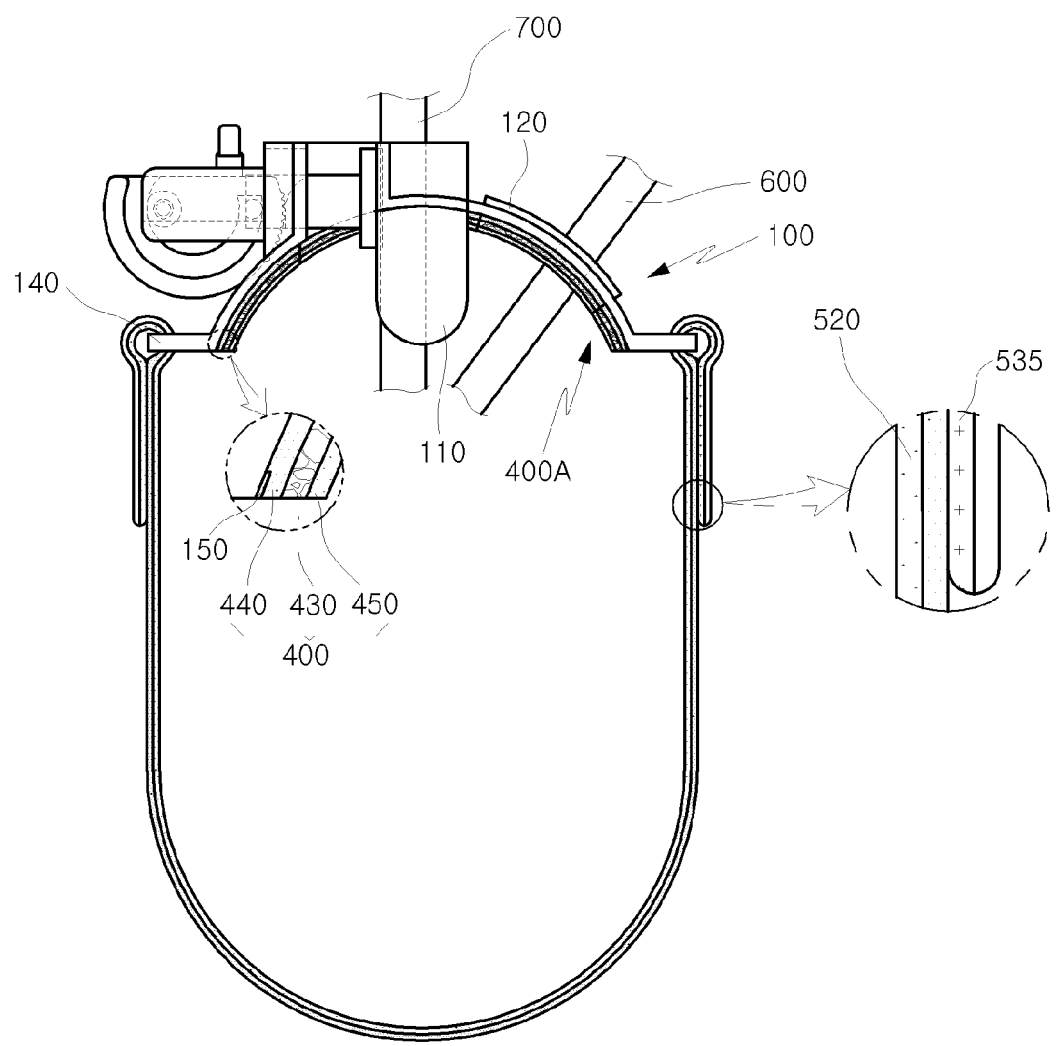
FIG. 16 is a sectional view illustrating the padding member and the holding member coupled to the body of the tracheal intubation tube fixing device having the suction tube insertion opening.

As shown in FIGS. 1 to 16, the tracheal intubation tube having a suction tube insertion opening according to a preferred embodiment of the present invention comprises a semi-arcuate body 100 configured to surround the patient's face and mouth. The body 100 is provided at an inner surface thereof with an airway securing block 110 to be inserted into the patient's mouth.

The body 100 has a suction tube insertion opening 120 perforated in a side position thereof for the insertion of a suction tube 600, and also has an intubation tube insertion hole 130 perforated in a center position thereof for the insertion of an intubation tube 700. The body 100 is also perforated with band fixing holes 140 for the coupling of a holding member 500 to prevent the body 100 from being moved from an accurate wearing position thereof.

The tracheal tube fixing device further comprises a pivotal fixing member 200 used to fix the intubation tube 700 inserted into the intubation tube insertion hole 130. To assure free entrance and exit of the pivotal fixing member 200 into and out of the insertion hole 130, a coupling structure 300 is provided to be coupled with the pivotal fixing member 200.

The pivotal fixing member 200 includes a pivoting piece 210 and a fixing piece 250. The pivoting piece 210 has a first pivoting contact surface 215, a semi-arcuate guide groove 220 recessed in a surface thereof to be opened at one end thereof, a coupling protrusion 225 formed at the same surface as the guide groove 220 to be positioned eccentric to the center thereof, and a pivoting grip 230 formed at a lower end thereof.

The fixing piece 250 is divided into a body piece 265 and a contact piece 280. The body piece 265 has a pivoting shaft 255 to be coupled with an inner circumferential wall 235 of the guide groove 220 and a second pivoting contact surface 260 to come into close contact with the first pivoting contact surface 215 in a pivoting direction of the pivoting piece 210. To be coupled with the body piece 265, the contact piece 280 has a coupling hole 275 such that a coupling head 270 protruding from the body piece 265 is fitted into the coupling hole 275.

The coupling structure 300 includes a pair of coupling shafts 340 having first and second coupling holes 310 and 320, respectively, and a coupling bar 330 to be penetrated through the first and second coupling holes 310 and 320. If the coupling protrusion 225 of the pivotal fixing member 200 is inserted into a space between the first and second coupling holes 310 and 320 such that it is linearly aligned with the first and second coupling holes 310 and 320, the coupling protrusion 225 is able to be coupled with the first and second coupling holes 310 and 320 as the coupling bar 330 is penetrated through the first and second coupling holes 310 and 320. The coupling structure 300 further includes an insertion wall portion 360 defining the insertion hole 130 for the intubation tube 700, the insertion wall portion 360 having a guide hole 350 perforated in a position thereof between the shafts 340, to facilitate entrance and exit of the body piece 265. The insertion wall portion 360 has a predetermined height starting from a plane having the insertion hole 130.

More particularly, the first pivoting contact surface 215 of the pivoting piece 210 is formed with a plurality of first corrugations 240, to prevent unwanted movement of the pivoting piece 210 when the pivoting piece 210 is pivotally rotated to come into close contact with the intubation tube 700 so as to fix the tracheal tube 700. The first corrugations 240 also allow the pivoting piece 210 to comply with the size of various tracheal tubes, so as to assure the close contact/fixing of the intubation tube 700 and the pivoting piece 210. The second pivoting contact surface 260 to come into contact with the first pivoting contact surface 215 is similarly formed with a plurality of second corrugations 245 to be engaged with the first corrugations 240. This assures the more close contact/fixing of the intubation tube 700 and the fixing piece 250.

The contact piece 280 serves to maintain the circular shape of the intubation tube 700 when the intubation tube 700 comes into close contact with and is fixed by the pivotal fixing member 200. In this case, to facilitate the close contact/fixing of the circular intubation tube 700, a contact surface of the contact piece 280 is recessed concavely to have a contact recess 285. Meanwhile, the insertion hole 130 is opened at a peripheral position thereof, to facilitate the insertion of the intubation tube 700.

The suction tube insertion opening 120 has a heart shape to improve the outer appearance of the tube fixing device. The airway securing block 110 is made of a micro-foam material to prevent any injury on the patient's teeth and mouth caused when the airway securing block 110 is inserted into the patient's mouth for the purpose of securing an airway in the respiratory tract.

Preferably, the micro-foam material is micro-cellular-poly-urethane-foam as a kind of polymer compound. The micro-cellular-poly-urethane-foam is soft to the touch and has a heat-insulation function.

As known, polymers have chemical, physical, and electrical properties available to a human being, and can be widely used for a variety of purposes. Since thermosetting or thermoplastic polymers are deformable prior to being hardened chemically at a high temperature, they can be used to fabricate various shapes of plastic products. Some of polymers have an extremely complex geometrical shape, and are processed rapidly with relatively simple techniques. The utility and advantageous effects of polymers and plastics on the modern life can be maximized by manufacturing appropriate shapes of plastic products using unique properties of plastics and due to the technical development and marketability and liquidity thereof.

The body 100 is provided, at both ends of the inner surface thereof, with a pair of Velcro tapes 150, and a padding member 400A is attached, at a surface thereof, to the Velcro tapes 150. The holding member 500, which will closely surround the patient's rear neck, is coupled to the body 110 as both ends thereof are fitted into the band fixing holes 140 of the body 100. The holding member 500 serves to keep the body 100 at a fixed position so as not to be moved from an accurate wearing position thereof.

The padding member 400A includes a padding body portion 400, which has a suction tube insertion hole 460 perforated in a position corresponding to the suction tube insertion opening 120 for the insertion of the suction tube 600, an airway securing block penetrating hole 410 for the penetration of the airway securing block 110, and an intubation tube insertion hole 420 perforated in a position corresponding to the insertion hole 130 for the intubation tube 700, the periphery of the intubation tube insertion hole 420 being opened at a peripheral position thereof.

The padding body portion 400 of the padding member 400A has a plurality of layers. The plurality of layers include an air-permeable sponge layer 430 to absorb a pressure applied from the body 100 to the patient's face and mouth, and an air-permeable non-woven fabric seating layer 440 attached to one surface of the sponge layer 430 to be seated on the inner surface of the body 100.

The plurality of layers further include an air-permeable non-woven fabric contact layer 450 attached to the other surface of the sponge layer 430 to come into contact with the patient's face and mouth. The contact layer 450 of the padding member 400A has a plurality of vent holes 455 to increase the air permeability of the padding member 400A in a state wherein the padding member 400A comes into contact with the patient's face and mouth, thereby reducing an unpleasantness due to impurities caused during a medical treatment and preventing skin problems.

The holding member 500 includes a body portion 510 to closely surround the patient's rear neck, and a pair of supporter portions 520 extending from both ends of the body portion 510 by a predetermined length.

A connector 530 is provided at one end of each supporter portion 520, to be fitted into to an associated one of the band fixing holes 140 of the body 100. The body portion 510 and the supporter portion 520 of the holding member 500 are formed by laminating air-permeable non-woven fabrics in multiple layers, to prevent skin problems caused while the holding member 500 closely surrounds the patient's rear neck and to provide the patient with a mental stability when wearing. The connector 530 of the holding member 500 has one end coupled to one end of the supporter portion 520. The other end of the connector 530 is provided at a surface thereof with a Velcro tape 535 such that the other end of the connector 530 can be attached to a surface of the supporter portion 520 after being fitted into the band fixing hole 140 of the body 100. Accordingly, the holding member 500 fixes the body 100 at an accurate wearing position suitable for securing an airway in the patients respiratory tract.

Now, the use state of the tracheal intubation tube fixing device having the suction tube insertion opening according to the present invention having the above described configuration will be described.

In use, to secure an airway in the patient's respiratory tract and to induce an artificial respiration of a serious patient in the intensive care unit and the respiration of a patient under a general anesthesia operation, the semi-arcuate body 100 is rapidly put on the patient's face by an operator, and the airway securing block 110 formed at the body 100 is inserted into the patient's mouth, so as to secure a sufficient airway in the patient's respiratory tract.

Thereafter, both the ends of the holding member 500 are fitted into the band fixing holes 140 formed in the body 100 to surround the patient's rear head such that the body 100 is kept at a fixed position on the patient's face.

In this case, to prevent the body 100 from being moved on the patient's face, the connectors 530 of the holding member 500 are firmly attached to the supporter portions 520 of the holding member 500 after passing through the band fixing holes 140 of the body 100.

After fixedly keeping the body 100 on the patient's face, the operator has to rapidly insert the intubation tube 700 into the patient's respiratory tract through the insertion hole 130 of the body 100. In this case, since the airway securing block 110 of the body 100 is inserted into the patient's mouth to secure a sufficient airway in the respiratory tract, the intubation tube 700 can be rapidly and easily inserted into the respiratory tract.

To prevent the intubation tube 700, inserted into the respiratory tract, from being moved or separated by the patient's or operator's movement, the intubation tube 700 can be kept at a fixed position via appropriate pivotal rotation of the pivoting piece 210 of the pivotal fixing member 200.

In this case, since the first and second corrugations 240 and 245 formed at the pivotal fixing member 200 are engaged with each other, the intubation tube 700 can be firmly fixed.

Meanwhile, it should be noted that secretion such as phlegm, etc. is caused in the patient's trachea while the intubation tube 700 is inserted to secure an airway in the patient's respiratory tract, and may close the patient's respiratory tract and threaten the patient's life. Therefore, it is essential to insert the suction tube 600 for suctioning the secretion such as phlegm, etc. into the trachea. In the present invention, the suction tube 600 can be inserted through the suction tube insertion opening 120 formed in the body 100, to rapidly remove the secretion such as phlegm, etc., for the sake of protecting the patient's life. In this case, the intubation tube 700 and the suction tube 600 can be simultaneously inserted, to enable rapid implementation of their different operations.

The padding member 400A is seated on the inner surface of the body 100 by the Velcro tapes 150, and the sponge layer 430 of the padding member 400A absorbs a pressure applied from the body 100 to the patient's face and mouth, to prevent any injury on the patient's face and mouth.

Also, since the contact layer 450 of the padding body portion 400, which comes into direct contact with the patient's mouth, has the plurality of vent holes 455, it is possible to reduce an unpleasantness due to impurities caused during a medical treatment and to prevent skin problems.

The body portion 510 and the supporter portions 520 of the holding member 500 are made of non-woven fabric layers stacked in multiple layers, to prevent skin problems caused while the holding member 500 closely surrounds the patient's rear neck and to provide the patient with a mental stability when wearing.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A tracheal intubation tube fixing device having a suction tube insertion opening for securing an airway in the patient's respiratory tract, the device comprising:
   a body configured to surround the patient's face and mouth and including an airway securing block to be inserted into the mouth, the suction tube insertion opening for the insertion of a suction tube, an intubation tube insertion hole for the insertion of an intubation tube, and band fixing holes;
   a pivotal fixing member to maintain the intubation tube, inserted into the intubation insertion hole, at a fixed position;
   a coupling structure to be coupled with the pivotal fixing member so as to assure free entrance and exit of the pivotal fixing member into and out of the intubation insertion hole;
   a padding member having a surface to be attached to Velcro tapes provided at both ends of the body; and
   a holding member configured to closely surround the patient's rear neck, the holding member being coupled to the body as being fitted, at both ends thereof, into the band fixing holes to prevent the body from being moved from a wearing position thereof.

2. The device according to claim 1, wherein the pivotal fixing member comprises:
   a pivoting piece having a first pivoting contact surface formed along an outer periphery thereof, a semi-arcuate guide groove recessed in a surface thereof to be opened at one end thereof, a coupling protrusion formed at the same surface as the guide groove to be positioned eccentric to the center thereof, and a pivoting grip formed at a lower end thereof; and
   a fixing piece including a body piece and a contact piece closely coupled with each other, the body piece having a pivoting shaft to be coupled with an inner circumferential wall of the guide groove and a second pivoting contact surface to come into close contact with the first pivoting contact surface in a pivoting direction of the pivoting piece, and the contact piece having a coupling hole to be coupled with a coupling head protruding from the body piece.

3. The device according to claim 1, wherein the coupling structure comprises:
   a pair of coupling shafts having first and second coupling holes, respectively;
   a coupling bar to be penetrated through the first and second coupling holes, if the coupling protrusion of the pivotal fixing member being inserted into a space between the first and second coupling holes, the coupling protrusion being coupled with the first and second coupling holes by means of the coupling bar penetrated through the first and second coupling holes; and
   an insertion wall portion defining the intubation tube insertion hole and having a guide hole perforated in a position thereof between the shafts, to facilitate entrance and exit of the body piece, the insertion wall portion having a predetermined height starting from a plane having the insertion hole.

4. The device according to claim 2,
   wherein the first pivoting contact surface of the pivoting piece is formed with a plurality of first corrugations, to prevent unwanted movement of the pivoting piece when the pivoting piece is pivotally rotated to come into close contact with the intubation tube for the fixing of the tracheal tube and to assure the close contact/fixing of the pivoting piece with various sizes of the tracheal tube, and
   wherein the second pivoting contact surface to come into contact with the first pivoting contact surface is formed with a plurality of second corrugations to be engaged with the first corrugations, so as to assure the close contact/fixing of the intubation tube and the fixing piece.

5. The device according to claim 2, wherein the contact piece serves to maintain the circular shape of the intubation tube when the intubation tube comes into close contact with and is fixed by the pivotal fixing member, and comprises a contact recess to facilitate the close contact/fixing of the circular intubation tube.

6. The device according to claim 3, wherein the intubation tube insertion hole is opened at a peripheral position thereof to facilitate the insertion and close contact/fixing of the intubation tube.

7. The device according to claim 1, wherein the suction tube insertion opening has a heart shape.

8. The device according to claim 1, wherein the airway securing block is made of a micro-foam material to prevent any injury on the patient's teeth and mouth caused when the airway securing block is inserted into the patient's mouth for the purpose of securing an airway in the respiratory tract.

9. The device according to claim 1, wherein the padding member includes a padding body portion comprising:
   a suction tube insertion hole perforated in a position thereof corresponding to the suction tube insertion opening for the insertion of the suction tube;
   an airway securing block penetrating hole for the penetration of the airway securing block; and
   an intubation tube insertion hole perforated in a position thereof corresponding to the intubation tube insertion hole of the body, the intubation tube insertion hole of the padding body portion being opened at a peripheral position thereof.

10. The device according to claim 9, wherein the padding body portion of the padding member includes a plurality of layers, the plurality of layers comprising:
    an air-permeable sponge layer to absorb a pressure applied from the body to the patient's face and mouth;
    an air-permeable non-woven fabric seating layer attached to one surface of the sponge layer, to be seated on the inner surface of the body; and
    an air-permeable non-woven fabric contact layer attached to the other surface of the sponge layer, to come into contact with the patient's face and mouth.

11. The device according to claim 10, wherein the contact layer of the padding member has a plurality of vent holes.

12. The device according to claim 1, wherein the holding member comprises:
    a body portion to closely surround the patient's rear neck;

a pair of supporter portions extending from both ends of the body portion by a predetermined length; and a pair of connectors provided at one end of the respective supporter portions, to be fitted into to the band fixing holes of the body.

13. The device according to claim 12, wherein each connector of the holding member has one end coupled to one end of the associated supporter portion and the other end provided at a surface thereof with a Velcro tape such that the other end of the connector is attached to a surface of the supporter portion after being fitted into the associated band fixing hole of the body.

14. The device according to claim 12, wherein the body portion and the supporter portions of the holding member are formed by laminating air-permeable non-woven fabrics in multiple layers.

15. The device according to claim 14, wherein each connector of the holding member has one end coupled to one end of the associated supporter portion and the other end provided at a surface thereof with a Velcro tape such that the other end of the connector is attached to a surface of the supporter portion after being fitted into the associated band fixing hole of the body.

* * * * *